United States Patent
Pieringer et al.

(10) Patent No.: US 10,682,201 B2
(45) Date of Patent: Jun. 16, 2020

(54) APPARATUS FOR INKING A SURGICAL INSTRUMENT

(71) Applicant: VISCOT MEDICAL, LLC, East Hanover, NJ (US)

(72) Inventors: Gary Pieringer, Shrewsbury, NJ (US); Matthew Levine, Selden, NY (US)

(73) Assignee: VISCOT MEDICAL, LLC, East Hanover, NJ (US)

( * ) Notice: Subject to any disclaimer, the term of this patent is extended or adjusted under 35 U.S.C. 154(b) by 41 days.

(21) Appl. No.: 15/888,802

(22) Filed: Feb. 5, 2018

(65) Prior Publication Data

US 2018/0221107 A1  Aug. 9, 2018

Related U.S. Application Data

(60) Provisional application No. 62/455,204, filed on Feb. 6, 2017.

(51) Int. Cl.
| | | |
|---|---|---|
| *A61B 17/00* | (2006.01) | |
| *A61B 90/00* | (2016.01) | |
| *B43L 25/00* | (2006.01) | |

(52) U.S. Cl.
CPC ........ *A61B 90/39* (2016.02); *A61B 2090/395* (2016.02); *A61B 2090/3916* (2016.02); *B43L 25/008* (2013.01)

(58) Field of Classification Search
CPC ................................................... B43L 25/008
USPC .................................................... 401/10, 11
See application file for complete search history.

(56) References Cited

U.S. PATENT DOCUMENTS

| | | | | |
|---|---|---|---|---|
| 1,559,274 | A | * | 10/1925 | Morris .................... B43L 25/02 222/80 |
| 5,641,078 | A | * | 6/1997 | Kaufmann ............ B43L 25/008 15/257.075 |
| 5,880,779 | A | | 3/1999 | Rhynes |
| 2006/0090658 | A1 | | 5/2006 | Phillips |
| 2013/0158481 | A1 | | 6/2013 | Taylor |
| 2013/0160574 | A1 | | 6/2013 | Kacian |

FOREIGN PATENT DOCUMENTS

EP  1 524 201 A1  4/2005

OTHER PUBLICATIONS

International Search Report and Written Opinion dated Jun. 26, 2018 for PCT Application No. PCT/US2018/016940.

* cited by examiner

*Primary Examiner* — David J Walczak
*Assistant Examiner* — Joshua R Wiljanen
(74) *Attorney, Agent, or Firm* — Moser Taboada; Alan Taboada (57) ABSTRACT

An apparatus for inking a surgical instrument includes an inking capsule, which comprises a base and a vertical wall extending from the base to define a cavity. The inking capsule has a first opening opposite the base, an ink reservoir disposed within the cavity, where the ink reservoir has ink disposed therein. The ink reservoir comprises a second opening proximate a top portion of the ink reservoir, and a penetrable seal covering the second opening to seal the ink in the ink reservoir when the seal is in an unbroken state.

21 Claims, 5 Drawing Sheets

APPARATUS FOR INKING A SURGICAL INSTRUMENT

CROSS-REFERENCE TO RELATED APPLICATIONS

This application claims the benefit of U.S. Provisional Patent Application No. 62/455,204, filed on Feb. 6, 2017, which is herein incorporated by reference in its entirety.

FIELD

Embodiments of the present invention generally relate to apparatus for inking surgical instruments.

BACKGROUND

During some surgical procedures, a doctor uses an awl to punch a hole in a bone of a patient, for example, to receive a screw or other hardware that is to be affixed to the bone. The inventors have discovered that sometimes there is difficulty in locating the hole after formation due to lack of contrast between the hole and surrounding tissue. Thus, the inventors believe that applying a visible mark to the patient bone proximate the hole, to increase visibility of the site of the hole, would be beneficial.

Thus, the inventors have provided an apparatus for inking a surgical instrument.

SUMMARY

Methods and apparatus for inking a surgical instrument are provided herein. In some embodiments, and apparatus for inking a surgical instrument includes: an inking capsule, comprising a base and a vertical wall extending from the base to define a cavity, the inking capsule having a first opening opposite the base; an ink reservoir disposed within the cavity, the ink reservoir having ink disposed therein and comprising a second opening proximate a top portion of the ink reservoir; and a penetrable seal covering the second opening to seal the ink in the ink reservoir when the seal is in an unbroken state.

In some embodiments, an apparatus for inking a surgical instrument includes: an inking capsule, comprising a base and a vertical wall extending from the base to define a cavity, the inking capsule having a first opening opposite the base; an ink reservoir disposed within the cavity, the ink reservoir having ink disposed therein and comprising a second opening proximate a top portion of the ink reservoir; a holder positioned immovably in the cavity of the inking capsule, the holder comprising a body dimensioned to receive the ink reservoir such that the ink reservoir is substantially immovable with respect to the holder, and at least one protrusion extending from the body and engaged with the inking capsule to prevent lateral movement of the holder within the inking capsule; a seal made from an impermeable and penetrable material, the seal affixed to the first opening of the inking capsule and extending over the second opening of the ink reservoir and sealing the ink in the ink reservoir, the seal comprising an insertion region overlying the second opening, the insertion region defined by a visible indicating boundary, wherein the seal is penetrable by the surgical instrument using a nominal manual force to allow a portion of the surgical instrument to break through the seal within an insertion region and contact the ink dispersed in the substrate; and a cap made from rigid material for removably covering the inking capsule, wherein the cap covers the seal when the cap is positioned to cover the inking capsule.

In some embodiments, a method of inking a portion of a surgical instrument includes: aligning the surgical instrument with an apparatus for inking the surgical instrument, the apparatus comprising: an inking capsule having a cavity disposed therein and a first opening disposed over the cavity, an ink reservoir disposed within the cavity and having ink disposed therein, the ink reservoir comprising a second opening proximate the first opening of the ink reservoir, and a penetrable seal covering the second opening to seal the ink in the ink reservoir when the seal is in an unbroken state; breaking the seal with the surgical instrument; and contacting the portion of the surgical instrument with the ink disposed in the ink reservoir, causing the ink to be disposed on the portion of the surgical instrument.

Other and further embodiments of the present invention are described below.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

To facilitate understanding, identical reference numerals have been used, where possible, to designate identical elements that are common to the drawings. The drawings are not drawn to scale and may be simplified for clarity. Elements and features of one embodiment may be beneficially incorporated in other embodiments without further recitation.

DETAILED DESCRIPTION

Embodiments of an apparatus for inking an instrument for marking bone or tissue during surgery (hereinafter, also referred to as "surgical instrument" or "marking instrument") and methods for using same are provided herein. The embodiments include an inking apparatus in which the marking instrument is inserted for marking a portion, usually a tip, of the marking instrument. The inking apparatus comprises an ink reservoir comprising ink disposed therein. The ink reservoir is sealed, for example via a protective layer, such as a foil or a foil laminate forming a seal, which when in an unbroken state, keeps the ink hermetically sealed within the ink reservoir prior to use. In use, the tip (or the region required to be marked) of the marking instrument is pushed through the foil and into the ink reservoir, thus bringing the tip into contact with the ink disposed in the ink reservoir. Some ink is transferred onto the tip of the marking instrument. The marking instrument is removed from the apparatus, thus conveniently providing the marking instrument with an inked tip usable for marking bone or tissue as desired. The ink reservoir may be positioned within a rigid container or capsule for structural robustness during transportation, storage, and use, adding another layer of safety to prevent contamination of the ink, spillage, convenience of use, and the like. In such instances, additional structures for holding the ink reservoir immovably within the capsule are provided. Such additional structures may include a body (e.g., a sleeve) positioned around the ink reservoir to hold the ink reservoir immovably within the sleeve. Additional structures are provided to constrain movement of the sleeve within the capsule. Additional structures may also include one or more portions of the capsule that constrain the movement of the ink reservoir within the capsule, including a rigid holding cavity for receiving the ink reservoir. The open end of the ink reservoir is aligned with the open end of the capsule, and an impermeable, penetrable sealing layer seals both the capsule and the ink reservoir. A cap may be provided to protect the seal when the capsule is not in use.

Figure 1:
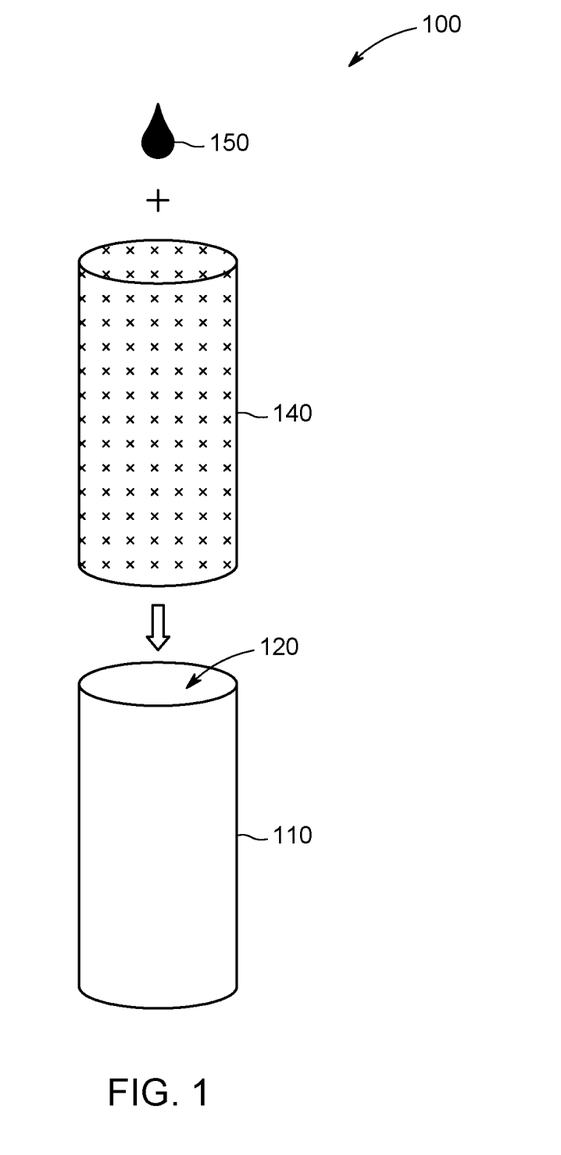
FIG. 1 depicts individual components of an ink reservoir in accordance with one or more embodiments of the invention.

FIG. 1 depicts individual components of an ink reservoir 100 in accordance with some embodiments of the invention. In some embodiments, the ink reservoir 100 comprises a shell 110, a substrate 140, and ink 150, which may be disposed in the substrate 140. The substrate 140 can generally be any suitable material for holding the ink 150 in a dispersed form across the body of the substrate 140. For example, the substrate 140 can be made of one or more of a permeable, foamed, porous, fibrous, or absorbent material, for example, to enable the substrate 140 to hold the ink 150. In some embodiments, the substrate 140 is felt, or a felt-like material, for example, produced by matting, condensing, and pressing natural or synthetic fibers. The substrate 140 has a height that is equal to or greater than the length of inking required or desired on the surgical instrument. For example, if a half inch of marking is desired on the marking instrument, then the substrate 140 has a height of at least one-half inch. Further, the substrate 140 allows movement of within the substrate, for example, the surgical instrument penetrates into the substrate 140 easily, to contact the ink 150 dispersed in the substrate 140.

The shell 110 comprises one or more walls defining a volume enclosed therein, the one or more walls surrounding an opening 120. The shell 110 can be made of any suitable material, such as one or more of a polymer, a metal, or a composite, and is generally impermeable by the ink 150. For example, in some embodiments, the shell 110 is a thin, flexible material wrapped around the permeable substrate 140. In some embodiments, the shell 110 comprises a flexible plastic sheet, such as polyester or the like, wrapped around the permeable substrate 140. In some embodiments, the shell 110 further comprises a base (not shown) opposite the opening 120, where the one or more walls extend from the base and terminate at the opening 120. The base prevents ink from leaking out of the bottom of the shell 110.

The ink 150 comprises a dye, such as gentian violet or similar approved dye, used for marking tissue or bone during surgical and/or diagnostic procedures, the dye dispersed in a suitable fluid (e.g. aqueous, gel) medium, or a medium that otherwise promotes the ink to be disposed on to the marking instrument. In some embodiments, the ink 150 is an ink approved by the Food and Drug Administration (FDA) for use in internal and/or external marking procedures in connection with surgery. In some embodiments, the ink 150 is dispersed in the substrate 140. In some embodiments, the ink 150 may be disposed in the ink reservoir without the substrate 140.

Figure 2:
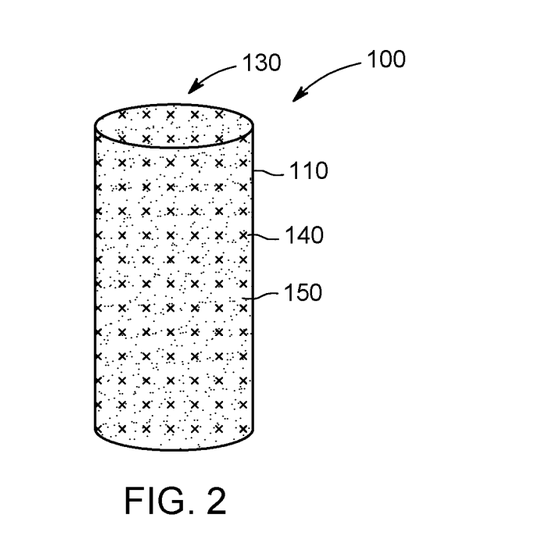
FIG. 2 depicts an ink reservoir in accordance with one or more embodiments of the invention.

FIG. 2 depicts an assembled ink reservoir 100, in accordance with one or more embodiments of the invention. The shell 110 includes an end 130 defining the opening 120, and may have an open or closed base opposite the open end 130. Alternatively, the end 130 may also be closed, however be penetrable by the marking instrument, to allow the instrument to be brought into contact with the ink 150, by piercing through the end 130.

Figure 3:
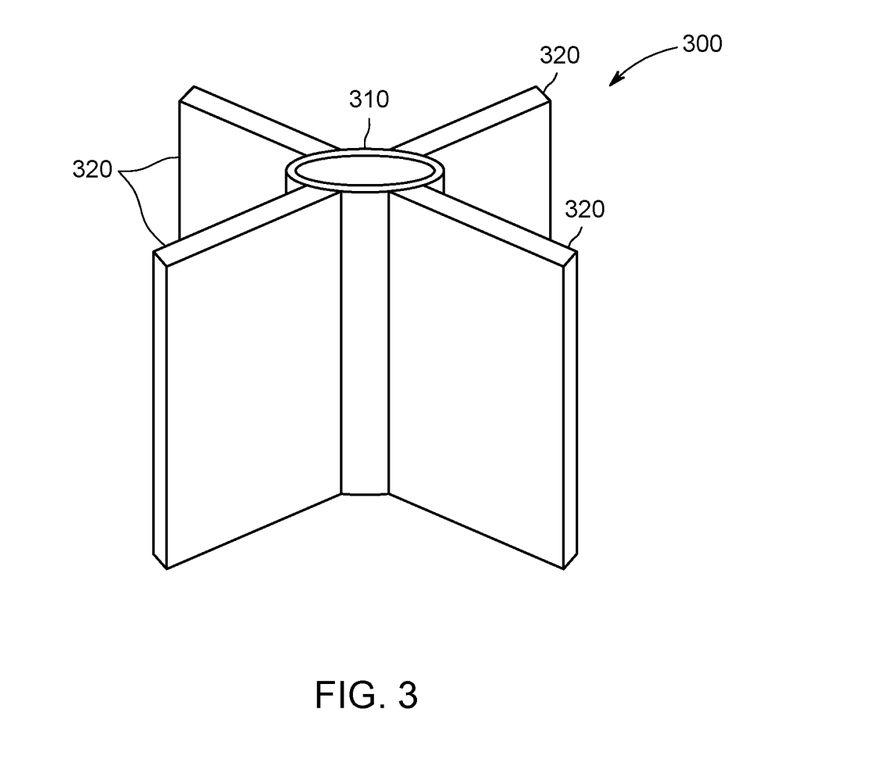
FIG. 3 depicts a holder for the ink reservoir of FIG. 2, in accordance with one or more embodiments of the invention.

FIG. 3 depicts a holder 300 for the ink reservoir of FIG. 2, in accordance with one or more embodiments of the invention. The holder 300 comprises a body 310 comprising a cavity for receiving the ink reservoir 100. The cavity may be sized to fit the ink reservoir 100 snugly therein, so as to constrain a lateral movement of the ink reservoir with respect to the body 310. In some embodiments, the body 310 may have a height that is equal to that of the ink reservoir 100. In some embodiments, the body 310 may have a height that is less than or greater than that of the ink reservoir 100. The combined arrangement of the holder 300 and the ink reservoir 100 positions the ink reservoir 100 opening 120 in an upright position for inking the surgical instrument during use (for example, immediately underneath a seal, as discussed below with respect to FIGS. 4A and 4B).

In some embodiments, the body 310 is connected to stabilizing protrusions 320, such as protrusions, wings, legs, arms, members, or the like, to stabilize the body 310 and the ink reservoir 100 inserted therein and to support the ink reservoir 100 in a desired orientation as discussed further below. For example, the protrusions 320 is sized to constrain lateral movement of the holder within a capsule, for example, as described with respect to FIG. 4A. The holder 300 may be made from one or more of polymer, composite or metal. In some embodiments, the stabilizing attachments are shaped differently from those shown the drawings. For example, instead of four protrusions 320, the holder 300 may comprise more or less protrusions, and/or differently shaped protrusions.

Figure 4A:
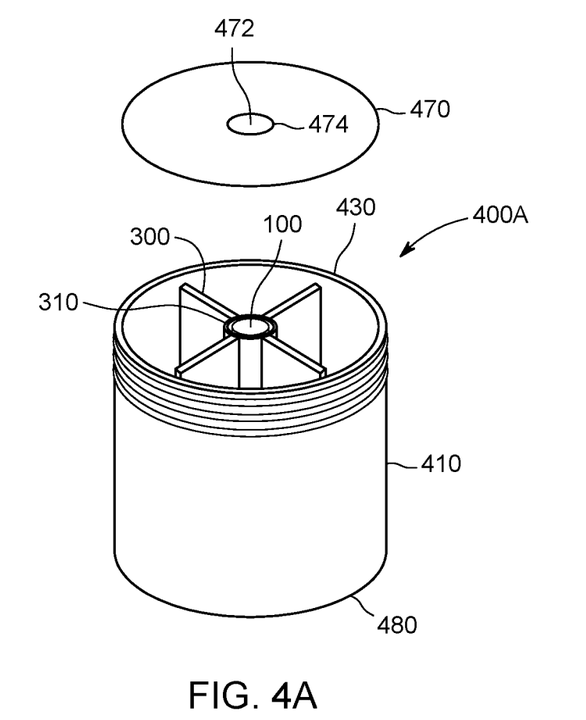
FIG. 4A depicts an isometric view of an inking capsule and an ink reservoir installed therein, in accordance with one or more embodiments of the invention.

FIG. 4A depicts an isometric view of an inking capsule 400A comprising the holder 300 of FIG. 3 having the ink reservoir 100 of FIG. 2 positioned within the capsule 400A, in accordance with one or more embodiments of the invention. FIG. 4A also depicts a seal 470 in an unassembled configuration with respect to the inking capsule 400A. The capsule 400A comprises a vertical wall 410 extending from a periphery of a base 480. The vertical wall 410 forms a (second) opening 430 opposite the base 480. For example, the capsule 400A has the form factor of a cylindrical jar. The capsule 400A may be formed using one or more of a polymer, a metal, or a composite, and provides physical protection to the ink reservoir 100, enhancing structural integrity of the ink reservoir 100, and thereby reducing the possibility of contamination of the ink or spillage of the ink.

In some embodiments, the protrusions 320 of the holder 300 are sized to contact the wall 410, to limit or prevent lateral movement of the holder 300, and thereby the ink reservoir 100, with respect to the capsule 400A. In some embodiments, the ink reservoir 100 has a height equal to or nearly equal to that of the capsule 400A such that the opening 120 of the ink reservoir 100 is approximately at the same height as the opening 430, when the ink reservoir 100 is positioned in the capsule 400A. In some embodiments (not shown), the holder 300 is shorter than the ink reservoir 100 such that a portion of the ink reservoir 100 projects out of the holder 300.

The seal 470 is made of a material suitable to form a barrier to retain the ink and to facilitate being pierced by a surgical instrument during an inking procedure. In some embodiments, the seal 470 comprises a metal foil, for example, an aluminum foil, and may further be laminated with a polymer or a composite, or any other suitable barrier material penetrable by a tip of a surgical instrument. The seal 470, when in an unbroken state, is penetrable or breakable by the tip of the surgical instrument using a nominal force (for example, manual force applied by a person, such as a surgeon or an assistant, or by a machine). In some embodiments, the nominal force is applied manually by a person without the aid of other tools. In some embodiments, the nominal force is applied by a person with the aid of other tools, such as a maul, a press, or the like. The seal 470 may be affixed along the opening 430 using an adhesive, ultrasonic welding, heat welding, or other attaching techniques to create a sealed capsule (discussed further with respect to FIG. 5A), comprising the wall 410 and the base 480 enclosed by the seal 470.

Optionally, the seal 470 includes an insertion region 472 defined or marked by a visible indicating boundary 474, such as a circular mark embossed or imprinted on the seal 470. The insertion region 472 is positioned above the opening 120 of the ink reservoir 100 when held in the capsule 400B. The insertion region 472 is sized to be equal to or smaller than the size of the opening 120 of the ink reservoir, and positioned to overlap with the opening 120. The insertion region 472 functions as a reliable guide for inserting the tip of the surgical instrument into the ink reservoir 100 for inking the tip. The indicating boundary 474 may or may not be circular, and may be in the shape of a logo, a design, or any other shapes such as ellipse, polygons, or other shapes as desired. The seal 470 can be broken within the insertion region 472, for example, by a surgical instrument so that the surgical instrument is inked by the ink 150 underneath.

Optionally, the seal 470 may be disposed only above the opening 120 and attached only to the ink reservoir 100 and/or the holder 300. Alternatively, the seal 470 may be disposed over the entire opening 430 but only penetrable in the region above the opening 120.

Figure 4B:
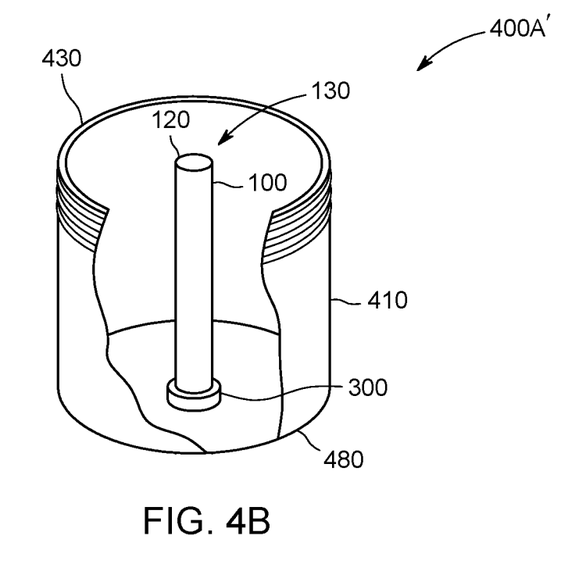
FIG. 4B depicts an isometric view of a partially cut away inking capsule showing an ink reservoir assembled thereto, in accordance with one or more embodiments of the invention.

FIG. 4B depicts an isometric view of a partially cut away inking capsule 400A' showing an ink reservoir 100 coupled thereto, in accordance with one or more embodiments of the invention. The holder 300 in the embodiment of FIG. 4A' comprises a cavity for receiving the ink reservoir 100 therein. The holder 300 is affixed to or formed as a part of the inking capsule 400A', and prevents lateral movement of the ink reservoir 100 positioned therein. The ink reservoir 100 has a height such that the first opening 120 of the ink reservoir is at either approximately or exactly the same level and alignment as the second opening 430 of the inking capsule 400A. Although not shown individually, the capsule 400A' may also be sealed using one or more sealing configurations discussed with respect to the seal 470 above.

Figure 5A:
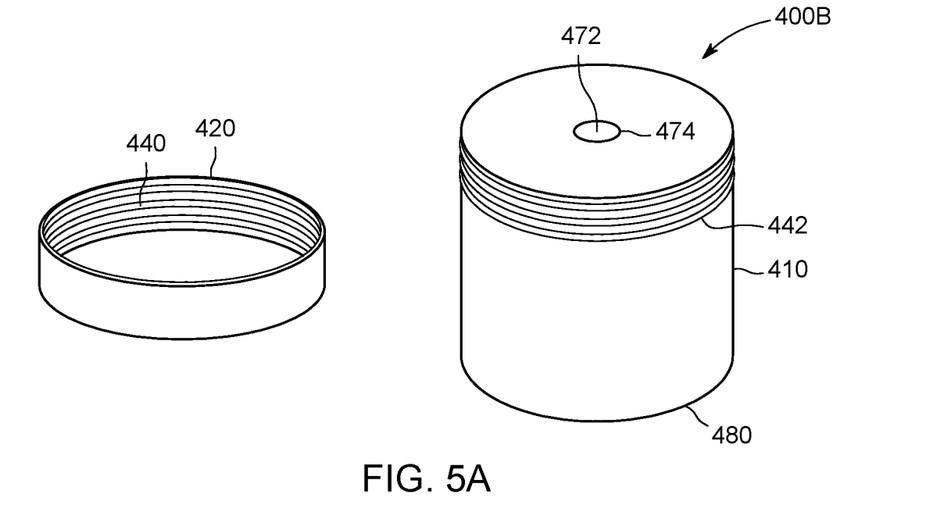
FIG. 5A depicts a sealed inking capsule with a cap removed, in accordance with one or more embodiments of the invention.

FIG. 5A illustrates a sealed capsule 400B with a cap 420 for providing a rigid protective cover for the capsule 400B, and particularly the seal 470, in accordance with one or more embodiments of the invention. The capsule 400B may be formed, for example, by sealing one of the capsules 400A or 400A' of FIG. 4A or 4B, respectively, using the sealing configurations discussed above. In some embodiments, the seal 470 also prevents a vertical motion of the ink reservoir 100 within the sealed capsule 400B. The cap 420 comprises screw threads 440 for mating with corresponding screw threads 442 on the wall 410. The cap 420 may be screwed on to the capsule 400B to form rigid enclosure for the enclosed ink reservoir 100. Alternatively, the cap 420 may be secured to the capsule 400B in other ways, such as by a press fit, a click fit, a hinged connection, clips or other fastening mechanisms, or the like. In some embodiments and as depicted in FIG. 5C, the cap 420 may include a third opening 502, such as a centrally disposed opening, sized to allow the tip of the surgical instrument to be inserted without removal of the cap 420. The opening 502 is aligned to be on top of and expose the insertion region 472 of the seal 470, such that the insertion region is accessible even with the cap 420 assembled onto the capsule 400B.

Figure 5B:
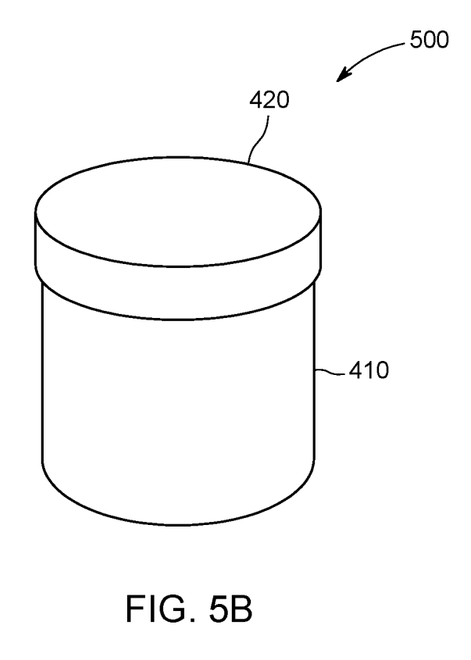
FIG. 5B depicts the inking capsule of FIG. 5A with the cap assembled on the inking capsule, in accordance with one or more embodiments of the invention.
Figure 5C:
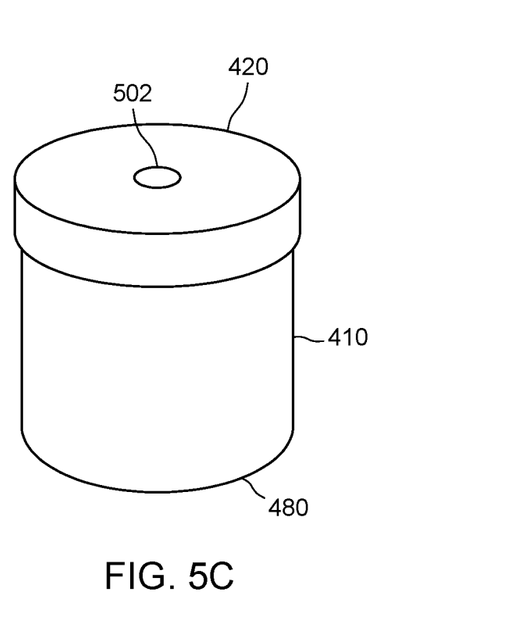
FIG. 5C depicts an assembled inking capsule having an opening in a cap, in accordance with one or more embodiments of the invention.
Figure 6A:
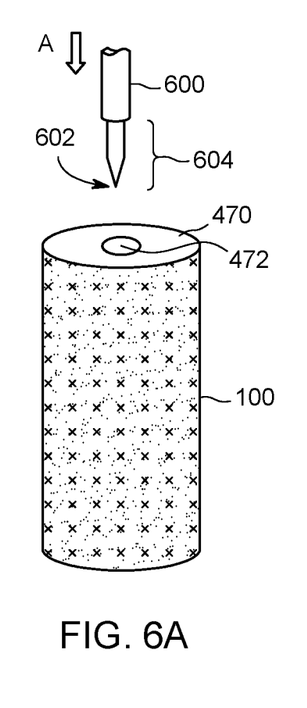
FIGS. 6A-C depict inking of a surgical instrument using the inking capsule in accordance with one or more embodiments of the invention.
Figure 6B:
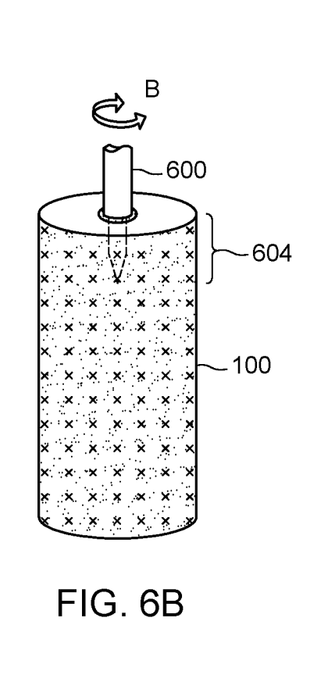
Figure 6C:
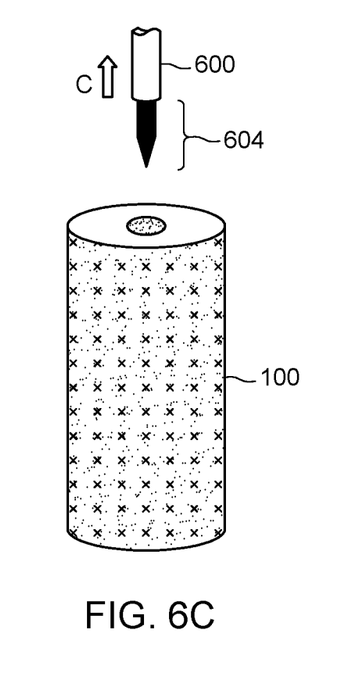

FIG. 5B illustrates an assembled inking capsule 500, comprising the cap 420 screwed onto the sealed capsule 400B, in accordance with some embodiments of the invention. The cap 420 of the capsule 500 may be removed to reveal a sealed capsule (for example, 400B), optionally having a marked insertion region (for example, 472) visible thereon. In one illustrative example of use, a surgeon unscrews the cap 420 off the capsule 500, and using the tip of the marking instrument, pierces the seal 470 (as shown in FIGS. 6A-C) in the insertion region 472, to ink the tip of the marking instrument. In some embodiments, for example, the embodiment of FIG. 5C, the tip of the marking instrument pierces the seal through the opening 502 without requiring that the cap 420 be unscrewed or removed. The capsule 500 prevents exposure of the ink to ambient agents, for example in the surgery room, and during transportation or storage, thereby preventing any contamination of the ink. For example, the components of the ink capsule may be formed of materials suitable to withstand sterilization procedures after assembly and sealing of the capsule. The procedure to ink the tip of the marking instrument as described above is convenient for a surgeon, involving only optionally removing the cap 420 off the capsule 500, and piercing the seal 470, where both operations require only a nominal force or effort on part of the surgeon, while ensuring that the ink is not contaminated. While the embodiments described herein illustrate cylindrical shapes of inking capsule 500 and the ink reservoir 100, either of the inking capsule or the ink reservoir may be built in different shapes, providing the same functionality.

FIGS. 6A-C depict inking of a surgical instrument 600 using the ink reservoir 100 encased in the capsule 500, in accordance with one or more embodiments of the invention. For ease of illustration, only the ink reservoir 100 is shown with a portion of the seal 470 covering the ink reservoir, and only a portion of the surgical instrument 600 comprising a tip 602 and a tip portion 604 for which inking is desired, is shown. The surgical instrument 600 is positioned to be inserted in the insertion region 472 by moving the surgical instrument in direction shown by arrow A in FIG. 6A. The insertion region 472 is punctured by the tip 602 of instrument 600 upon pushing the instrument 600 with a nominal force. The inserted portion of the instrument 600 contacts the ink 150 dispersed in the permeable substrate 140 of the ink reservoir 100, and the ink 150 is disposed on the inserted portion of the instrument 600. The instrument 600 is inserted to a depth equal to which inking is required, for example, up to a height of the tip portion 604. The ink reservoir 100 has a height equal to or greater than the height of the tip portion 604 to allow the instrument 600 to be inserted vertically into the ink reservoir 100 at least up to the height of the tip portion 604. The surgical instrument 600 may be twisted (rotated clockwise or anticlockwise) inside the permeable substrate 140 (as shown by arrow B) for uniform inking of the tip of the marking instrument inserted in the ink reservoir 100 (although simple insertion and removal may provide sufficiently uniform inking as well). Subsequently, as depicted in FIG. 6C, the surgical instrument 600 is removed from the permeable substrate 140 by pulling in direction generally opposite to the direction of insertion, for example, depicted by arrow C in FIG. 6C, yielding an inked tip portion 604, as depicted by the darkened shading. While a twisting action is shown in FIG. 6B, in some embodiments, only a simple insertion of FIG. 6A and pulling out of FIG. 6C is sufficient to ink the tip portion 604 of the marking instrument 600.

While embodiments specific to those described in the drawings are described, several variations are contemplated herein. In some embodiments, the holder does not have protrusions, and is instead affixed to the base 480. In some other embodiments, the ink reservoir 100 is affixed to the base 480 of the capsule 400A directly, without a holder 300. For example, in some embodiments, the capsule 400A is sized to enclose and fit the ink reservoir 100 therein without the use of a holder, or similar features may be formed in the capsule to provide the same function as the holder. In some embodiments, the seal 470 only seals the ink reservoir at the opening of the ink reservoir (for example, along opening 120), and does not extend beyond the ink reservoir 100 (for example, to the opening 430 of the capsule 400A as shown in FIG. 4A or the capsule 400A' as shown in FIG. 4B).

In addition, features shown in the various embodiments described above may be combined and/or modified by one of ordinary skill in the art without departing from the spirit and scope of the present invention. Thus, while the foregoing is directed to embodiments of the present disclosure, other and further embodiments of the disclosure may be devised without departing from the basic scope thereof.

The invention claimed is:

1. An apparatus for inking a surgical instrument, comprising:
   an inking capsule, comprising a base and a vertical wall extending from the base to define a cavity, the inking capsule having a first opening opposite the base;
   an ink reservoir disposed within the cavity, the ink reservoir having ink disposed therein and comprising a second opening proximate a top portion of the ink reservoir; and
   a penetrable seal covering the second opening to seal the ink in the ink reservoir when the seal is in an unbroken state, wherein the seal is destroyed when punctured.

2. The apparatus of claim 1, further comprising a holder for constraining lateral movement of the ink reservoir within the cavity, the holder comprising
   a body dimensioned to receive the ink reservoir and constrain lateral movement of the ink reservoir with respect to the body.

3. The apparatus of claim 2, wherein the holder is affixed to the inking capsule, the holder constraining lateral movement of the ink reservoir with respect to the inking capsule.

4. The apparatus of claim 2, wherein the holder further comprises at least one protrusion disposed between the body and the vertical wall of the inking capsule to prevent lateral movement of the holder within the inking capsule.

5. The apparatus of claim 1, wherein the seal is affixed to the first opening of the inking capsule.

6. The apparatus of claim 1, wherein the seal is affixed to the second opening of the ink reservoir.

7. The apparatus of claim 1, wherein the seal further comprises a visible indicating boundary defining an insertion region aligned with and over the second opening of the ink reservoir, wherein the size of the insertion region is equal to or smaller than the size of the second opening of the ink reservoir.

8. The apparatus of claim 7, further comprising a cap shaped to cover the first opening of the inking capsule and the seal thereon, the cap made from rigid material, wherein the cap further comprises a third opening aligned with the insertion region of the seal, such that when the cap is assembled to the inking capsule, the third opening allows access to the insertion region.

9. The apparatus of claim 1, further comprising a cap shaped to cover the first opening of the inking capsule and the seal thereon, the cap made from rigid material.

10. The apparatus of claim 1, wherein the ink reservoir further comprises a substrate disposed in a volume of the ink reservoir, the ink dispersed in the substrate, wherein the substrate allows movement of the surgical instrument into and within the substrate.

11. The apparatus of claim 1, wherein the penetrable seal comprises a metal foil.

12. The apparatus of claim 1, wherein the penetrable seal hermetically seals the ink in the ink reservoir when the seal is in the unbroken state.

13. An apparatus for inking a surgical instrument, comprising:
    an inking capsule, comprising a base and a vertical wall extending from the base to define a cavity, the inking capsule having a first opening opposite the base;
    an ink reservoir disposed within the cavity, the ink reservoir having ink disposed therein and comprising a second opening proximate a top portion of the ink reservoir;
    a penetrable seal covering the second opening to seal the ink in the ink reservoir when the seal is in an unbroken state; and
    a cap shaped to cover the first opening of the inking capsule and the seal thereon, the cap made from rigid material, wherein the cap includes a third opening that is aligned with the first and the second openings when the cap is disposed on the inking capsule.

14. An apparatus for inking a surgical instrument, comprising:
    an inking capsule, comprising a base and a vertical wall extending from the base to define a cavity, the inking capsule having a first opening opposite the base;
    an ink reservoir disposed within the cavity, the ink reservoir having ink disposed therein, and comprising a second opening proximate a top portion of the ink reservoir;
    a holder positioned immovably in the cavity of the inking capsule, the holder comprising a body dimensioned to receive the ink reservoir such that the ink reservoir is substantially immovable with respect to the holder, and at least one protrusion extending from the body and engaged with the inking capsule to prevent lateral movement of the holder within the inking capsule;

a seal made from an impermeable and penetrable material, the seal affixed to the first opening of the inking capsule and extending over the second opening of the ink reservoir and sealing the ink in the ink reservoir, the seal comprising an insertion region overlying the second opening, the insertion region defined by a visible indicating boundary, wherein the seal is penetrable by the surgical instrument allow a portion of the surgical instrument to break through the seal within an insertion region and contact the ink; and a cap made from rigid material for removably covering the inking capsule, wherein the cap covers the seal when the cap is positioned to cover the inking capsule.

15. The apparatus of claim 14, further comprising a substrate disposed in a volume of the ink reservoir and having the ink dispersed in the substrate, wherein the substrate allows movement of the surgical instrument into and within the substrate.

16. The apparatus of claim 14, wherein the cap includes a third opening that is aligned with the first and second openings when the cap is disposed on the inking capsule.

17. A method of inking a portion of a surgical instrument, the method comprising:

aligning the surgical instrument with an apparatus for inking the surgical instrument, the apparatus comprising:

an inking capsule having a cavity disposed therein and a first opening disposed over the cavity, an ink reservoir disposed within the cavity and having ink disposed therein, the ink reservoir comprising a second opening proximate the first opening of the ink reservoir, and a penetrable seal covering the second opening to seal the ink in the ink reservoir when the seal is in an unbroken state;

breaking the seal with the surgical instrument, wherein the seal is destroyed when punctured; and contacting the portion of the surgical instrument with the ink disposed in the ink reservoir, causing the ink to be disposed on the portion of the surgical instrument.

18. The method of claim 17, wherein the contacting further comprises twisting the portion of the surgical instrument within the ink reservoir.

19. The method of claim 17, further comprising:

removing a cap of the apparatus for inking the surgical instrument to reveal the penetrable seal prior to breaking the seal.

20. The method of claim 17, further comprising:

moving the portion of the surgical instrument through an opening formed in a cap of the apparatus for inking the surgical instrument to break the penetrable seal without removing the cap.

21. The method of claim 17, further comprising:

aligning the portion of the surgical instrument with an indicating boundary visible over an insertion region of the penetrable seal prior to breaking the seal.

* * * * *